United States Patent
Wells

(10) Patent No.: US 12,311,007 B2
(45) Date of Patent: May 27, 2025

(54) HERBAL PRODUCTS AND METHODS FOR TETRAHYDROCANNABINOL (THC) DETOXIFICATION

(71) Applicant: Shonneka Wells, West Palm Beach, FL (US)

(72) Inventor: Shonneka Wells, West Palm Beach, FL (US)

(*) Notice: Subject to any disclaimer, the term of this patent is extended or adjusted under 35 U.S.C. 154(b) by 0 days.

(21) Appl. No.: 18/651,875

(22) Filed: May 1, 2024

(65) Prior Publication Data

US 2024/0269213 A1    Aug. 15, 2024

Related U.S. Application Data

(62) Division of application No. 17/574,041, filed on Jan. 12, 2022, now abandoned.

(60) Provisional application No. 63/137,448, filed on Jan. 14, 2021.

(51) Int. Cl.
| | |
|---|---|
| A61K 36/42 | (2006.01) |
| A23L 33/105 | (2016.01) |
| A23L 2/60 | (2006.01) |

(52) U.S. Cl.
CPC .......... *A61K 36/42* (2013.01); *A23L 33/105* (2016.08); *A23L 2/60* (2013.01)

(58) Field of Classification Search
None
See application file for complete search history.

(56) References Cited

U.S. PATENT DOCUMENTS

| | | |
|---|---|---|
| 6,183,747 B1 | 2/2001 | Ren |
| 6,210,738 B1 | 4/2001 | Chen |
| 7,014,872 B2 | 3/2006 | Pushpangadan et al. |
| 8,993,008 B1 | 3/2015 | Mashat et al. |
| 9,034,400 B2 | 5/2015 | Sharma et al. |
| 10,004,757 B1 | 6/2018 | Vining |
| 10,639,341 B2 | 5/2020 | Shetty |
| 10,675,319 B2 | 6/2020 | Lin et al. |
| 10,757,961 B2 | 9/2020 | Wu et al. |
| 2002/0025349 A1 | 2/2002 | Brindavanam et al. |
| 2020/0085904 A1 | 3/2020 | Subramoni et al. |
| 2021/0212929 A1* | 7/2021 | Greenbaum ........... A61K 9/146 |

FOREIGN PATENT DOCUMENTS

KR    20130066958 A    6/2013

OTHER PUBLICATIONS

Yuan (CN 105851404 A—English translation) 2016.*
Brand (Frontiers in Pharmacology (2017), vol. 8, article 108, 11 pages).*
Miller, Izzy, "The Truth About THC Drug Testing and How Long Cannabis Can Be Detected in the Body", Emerald Media—Cannabis News & Lifestyle Magazine, Jan. 27, 2021, 8pp.
Gunnars, Kris, "10 Evidence-Based Benefits of Green Tea", Healthline, Nutrition, Apr. 6, 2020, 16pp.
Ulbricht, Catherine, et al., "An Evidence-Based Systematic Review of Elderberry and Elderflower (*Sambucus nigra*) by the Natural Standard Research Collaboration" ResearchGate, Journal of Dietary Supplements—Jan. 2014, Informa Healthcare, 42pp.
Nagappan, Krishnaveni, et al., "Charantin: A Neglected Antidiabetic Compound from *Momordica charantia* L.", Int. J. Pharm. Sci. Rev. Res., 51(2), Jul.-Aug. 2018; Article No. 07, pp. 35-40, ISSN 0976-044X, 6pp.
Kaushik, Ujjwal, et al., "Cururbitacins—An insight into medicinal leads from nature", Pharmacognosy Review, Jan.-Jun. 2015; 9(17): 12-18, doi: 10.4103/0973-7847.156314, 14pp.
Hudson, Tori, Nutrient Profile: Bitter melon (*Momordica charantia*), Natural Medicine Journal, https://www.naturalmedicinejournal.com, Oct. 2012 vol. 4, Issue 10, 7pp.
M. Miro; Cucurbitacins and their Pharmacological Effects; Phytotherapy Research; 1995; pp. 159-168; vol. 9.
Chanda et al.; Determination of cucurbitacin E in some selected herbs of ayurvedic importance through RP-HPLC; Journal of Ayurveda and Integrative Medicine; 2018; pp. 287-293.
Zhu (International Journal of Molecular Sciences (2012), vol. 13, pp. 14203-14218).

* cited by examiner

*Primary Examiner* — Susan Hoffman
(74) *Attorney, Agent, or Firm* — Taft Stettinius & Hollister LLP

(57) ABSTRACT

The present invention relates to herbal teas and drinks and methods of using same for purging toxins in the bloodstream and urine of a subject. Such toxins include tetrahydrocannabinol (THC) and its metabolites.

8 Claims, No Drawings

HERBAL PRODUCTS AND METHODS FOR TETRAHYDROCANNABINOL (THC) DETOXIFICATION

CROSS-REFERENCE TO RELATED APPLICATIONS

The present application is a divisional of U.S. Nonprovisional application Ser. No. 17/574,041 filed on Jan. 12, 2022, now abandoned which claims the benefit of U.S. Provisional Application No. 63/137,448 filed on Jan. 14, 2021, which are incorporated herein by reference in its entirety.

FIELD OF THE INVENTION

The present invention relates to herbal teas and drinks and methods of using same for purging toxins in the bloodstream and urine of a subject. Such toxins include tetrahydrocannabinol (THC) and its detectable metabolites.

BACKGROUND OF THE INVENTION

Regular drug testing is a reality for many Americans. Numerous companies continue to check their employees for drugs such as marijuana, despite the fact that it is now legal in the majority of states. And, unfortunately, even if one lives in a state where recreational use is legal, a positive drug test could lead to being fired from a job.

Routine drug tests also continue to be part of legal system, often being required to monitor individuals on probation or as part of a judicial sentence.

More frequently, individuals consider or utilize home drug testing in anticipation of an upcoming drug screening, especially if they are unsure whether they will have issues with recent recreational use showing a positive result.

Home drug tests have become widely available from both local drug stores such as CVS and Walgreens, and online retailers. Kits are available for testing saliva, urine, and hair, although urine tests are by far the most common. These kits usually include a collection cup, the test itself (a strip, card, or cassette), and instructions for use. Some kits also contain shipping containers so that one can send a sample off to a laboratory for further testing if necessary. The laboratory will typically provide more detailed and accurate results.

Home kits (and even most employer-used kits) are generally qualitative, i.e. they indicate whether a particular substance is in an individual's system, and not exactly how much of any given substance is present, i.e. they are not quantitative. This is important because passing a drug screening (or not) will depend on the detectable cut-off levels for that particular drug. For example, for THC, the typical cut-off is 50 ng/ml.

If a home drug test is positive, and there is an official screening coming up, there are still various ways that individuals can attempt to increase their chances of passing. For example, other than using a synthetic or powdered urine to cheat the test, common methods include: i) stop using substances well before the anticipated drug test; ii) postponement of the official test if possible; iii) ingestion of extra water prior to testing in order to attempt to dilute the urine while simultaneously taking a vitamin B supplement to retain a natural yellow urine color; iv) providing a urine sample later in the day to avoid a more concentrated sample early in the morning; v) take the urine sample mid-stream; vi) stopping exercise activities at least 24 hours prior to the test as exercise releases THC metabolites from fat cells; vii) reducing calorie intake to reduce body fat; and, viii) utilizing a home detoxification product. However, home detoxification products are variable in terms of their effectiveness.

*Momordica charantia* is a tropical and subtropical vine of the family Cucurbitaceae, widely grown in Asia, Africa, the Caribbean, and the southern regions of the United States. It has a long history of use as a hypoglycemic agent, however, different parts of the plant are used medicinally to treat many disorders conditions in humans including: high blood pressure, diabetes (hyperglycemia), fever, skin fungal infections, gastrointestinal cramps, psoriasis, hyperlipidemia, hemorrhoids, glaucoma, infertility and gynecological conditions, viral infections and certain cancers. See for example: Hudson, (2012) "Nutrient Profile: Bitter Melon (*Momordica charantia*)," Natural Medicine Journal, vol. 4.

The four parts of the *Momordica charantia* plant include the vine, leaves, yellow flowers, and bitter melon fruit. The plant contains several substances that likely contribute to its effectiveness as a medicinal product. These include various alkaloids, glycosides and peptides.

The *Momordica charantia* plant also contains several unique compounds that are thought to possess pharmacological properties:

Cucurbitin belongs to a family of structurally diverse triterpenes found in the members of Cucurbitaceae and several other plant families that are known to have immense pharmacological potential. See Kaushik et al., (2015) "Cucurbitacins—An Insight into Medicinal Leads from Nature," Pharmacogn Rev. 9(17): pp. 12-18. Charantin is a natural steroidal glycoside present in the fruits of the plant and has been reported to possess potential hypoglycemic or anti-diabetic activity. See Nagappan et al., (2018) "Charantin: A Neglected Antidiabetic Compound from *Momordica Charantia* L.," Int. J. Pharm. Sci. Rev. Res., 51(2), pp35-40. Cucurbitacin, contained abundantly in *Momordica charantia*, is a bitter tasting compound that has been isolated from other members of the family Cucurbitaceae, such as cucumber and melon. Cucurbitacin exhibits anti-cancer activity and is also used for the treatment of hepatic disease in traditional Chinese medicine. Cucurbitacin has a broad range of pharmacological properties including purgative, hepatoprotective, antifungal, anti-inflammatory, cytotoxic, and antineoplastic activities. See Hudson 2012.

Momordin is one of several saponins derived from oleanolic acid and is a triterpenoid.

Momorcharins are a type-I ribosome inactivating protein that found in *Momordica charantia* and has shown to be effective against a broad range of human viruses as well as having antitumor activities. In addition, the *Momordica charantia* plant also contains several proteins which can serve as a fuel source. Further, the melon has been identified as the source of many of the above compounds. The melon's traditional use has included its use in gynecological disorders and for the treatment of infertility.

*Momordica charantia* is also known to have various purgative properties.

What is needed is a home detoxification product, preferably with substantial purgative properties that is effective in clearing an individual's system or urine of substances that can negatively impact an official or employment-related drug screening test.

SUMMARY OF THE INVENTION

The present application provides a THC detoxification product comprising an Herbal THC Detoxification Blend composed of a decoction of *Momordica charantia* blended into an herbal drink, or other beverage that when ingested within 24 hours of drug screening test, will eliminate all traceable THC metabolites for an individual's system such that a urine test will show up as negative.

In some embodiments, the Herbal THC Detoxification Blend includes additional ingredients such as herbs and other natural products. These additional ingredients have health benefits on their own and provide a way to cleanse the bloodstream of THC, boost endurance and stamina, allowing THC users to have the cognitive function to perform daily life duties.

Embodiments of the current invention include carefully chosen blend of herbs that work together to detoxify the body of harmful toxins, therefore increasing energy, vitality, and stamina. Additional benefits include increased mental awareness and focus, increased endurance, weight loss, cold and flu relief.

Other embodiments of the current invention include methods of preparing the Herbal THC Detoxification Blend. Still other embodiments are drawn to methods of using the Herbal THC Detoxification Blend in order to clear an individual's system of detectable THC metabolites.

More specifically, an embodiment of the current invention includes a composition for the removing tetrahydrocannabinol or its metabolites from an individual's bloodstream and urine comprising an aqueous decoction of the plant *Momordica charantia*, In another embodiment, the composition for the removing tetrahydrocannabinol or its metabolites from an individual's bloodstream and urine comprises a solution made from the *Momordica charantia* which has been dried and ground.

In other embodiments of the invention the compositions made from the *Momordica charantia* plant further comprise water and one or more herbs or other natural products.

In still other embodiments of the current invention, the compositions made from the *Momordica charantia* plant include one or more of an herb or other natural products is selected from the group consisting of the fruit of the *Momordica charantia* plant, elder flower, dandelion root, green tea leaves, lemon balm, lemon peel, and crystalized ginger root.

In any of the embodiments of the current invention, the compositions can include a sweetener.

Another embodiment of the current invention is drawn to a method for removing tetrahydrocannabinol or its metabolites from an individual's bloodstream and urine comprising ingesting any one of the *Momordica charantia* plant compositions described herein.

In any embodiment of the current invention, the amount of the *Momordica charantia* plant composition ingested is based upon the body weight of the individual.

In any embodiment of the current invention, the *Momordica charantia* plant composition is ingested one or more times over a period of four hours.

In yet other embodiments of the current invention, the *Momordica charantia* plant composition is ingested one or more times within a 24 to 48 hour period or until THC or its detectable metabolites are not detected in the urine or other sample form the individual.

In any of the methods of the current invention, the efficacy for removing tetrahydrocannabinol or its metabolites from an individual's bloodstream and urine is monitored using a home drug testing kit.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION OF THE INVENTION

The current invention is drawn to an Herbal THC Detoxification Blend that can be incorporated into a tea or other suitable beverage. The current invention includes a first step of decocting the fresh *Momordica charantia* plant including the vines, leaves, whole fruit to make an an extraction which possesses purgative properties. Various other ingredients are also added, for example, lemon peel which, among other things, balances the flavor of the brewed decoction.

As a second step of the current invention, blend of herbs are added to the *Momordica charantia* decoction in order to accomplish, among other things, a boost of the functionality of the detoxification which in addition to cleansing THC and detectable metabolites from the bloodstream and urine, can increase mental awareness and focus, increased endurance, relieving sinusitis, cold relief and much more.

Various embodiments of the invention also include the bottling the initial brewed blend of the *Momordica charantia* plant with sweeteners or alternatively, packaging individual servings of dried herbal blend as a loose leaf tea blend using sachets or tea bags

Aqueous Decoction of *Momordica charantia*

In a non-limiting example of the current invention, an aqueous decoction of the *Momordica charantia* is made. The entire *Momordica charantia* plant is used (typically about 14 total grams. The yellow flowers are not used.

As a person of skill in the art would be aware, "decoction" is a method of extraction by boiling herbal or plant material to dissolve the chemicals of the material, which may include stems, roots, bark and rhizomes.

Decoction of the *Momordica charantia* to make the Herbal THC Detoxification Blend involves first separating fresh or previously frozen plants into approximate 14-20 g bunches in which all fruit connected to vines are removed and then placed into large cloth bags. The plants in the bags are then mashed in the bags. The bitter melon fruit are then added back to the bag. The bags are then boiled in approximately 1800 ml distilled or spring water for about 15 min. The inventor has found that the boiling allows for the extraction of oils, volatile organic compounds and various chemical substances from the plant.

The resulting solution is strained to remove the plant and lemon slices and any other remaining particles. For example, a sliced whole lemon can be added for taste. The resulting mixture is and strained 5-10 times to remove any excess particles. Further, once the decoction solution is strained, other ingredients can be added. As a non-limiting example, a sweetener such as stevia is added to improve the taste of the decoction. It is contemplated that the amount and type of sweetener can be varied according to individual preferences. The resulting decoction solution is typically 1500 ml. This typically yields three 500 ml detoxification doses.

Preparation of the Herbal THC Detoxification Blend

The Herbal THC Detoxification Blend can be made either from brewing the Dried *Momordica charantia* plant described above or directly from the Aqueous Decoction solution.

Importantly, the inventor has discovered that the inclusion of one or more additional herbs or other natural ingredients adds to the purgative benefits and provides additional health benefits in addition to improving taste and drinkability to the Herbal THC Detoxification Blend.

Non-limiting examples are described below:

| Ingredient | Traditional Use | Benefit to the Herbal Blend* |
|---|---|---|
| Elder Flower | used for swollen sinuses (sinusitis), cold and flu, bronchitis, diabetes, and constipation | Increases urine production |
| Dandelion Root | promotes healthy digestion, liver function, noted for its effectiveness to assist with hormone imbalance, stomach upset, fever and flu | Natural detoxification substance |
| Green tea leaves | Mood elevation, calmness, mental awareness and focus, increases metabolism and helps with weight loss, reduces cholesterol, promotes immune health, may have cancer prevention properties. | Improves taste; provides a pleasant vehicle |
| Lemon Balm | Traditionally used to improve mood and cognitive function, helps relieve stress, reduces anxiety, eases insomnia and sleep disorders, relive indigestion, minimize menstrual cramps | Calming effect; improves taste |
| Ginger Root (crystalized) | natural oil (gingerol); antioxidant and anti-inflammatory properties; promotes digestion, reduces nausea supports immune function. | Flavoring |
| Lemon Peel | D-limonene and Vitamin C thought to have antibacterial, antimicrobial, antifungal, antioxidant properties, may have anticancer properties; reduces risk of heart disease, D-limonene thought to lower blood sugar, triglyceride, and LDL cholesterol levels, while increasing HDL cholesterol | Flavoring |

See for example: Ulbricht et al., (2014) "An Evidence-Based Systematic Review of Elderberry and Elderflower (*Sambucus nigra*) by the Natural Standard Research Collaboration" J. Dietary Supplements, 11(1): pp. 80-120; Jedrejek et al., (2019) "Comparative phytochemical, cytotoxicity, antioxidant and haemostatic studies of *Taraxacum officinale* root preparations," Food Chem Toxicol 26: pp. 233-247; Gunnars, (2020) "Ten Evidence-Based Benefits of Green Tea," [www.healthline.com/nutrition/top-10 evidence-based-healthbenefits-of-green-tea]; Cronkleton, (2019) "Ten Benefits of Lemon Balm and How to Use It," [www.healthline.com/health/lemon-balm-uses]; Bode et al., (2011) "The Amazing and Mighty Ginger," In: Benzie et al., eds. *Herbal Medicine: Biomolecular and Clinical Aspects.* 2nd edition, Chapter 7, Boca Raton: CRC Press/Taylor & Francis; Lang, (2019) "Nine Benefits and Uses of Lemon Peel," [www.healthline.com/nutrition/lemon-peel].

As a non-limiting method, to produce a single serving of the Herbal THC Detoxification Blend, about 2.0-6.0 g of dehydrated *Momordica charantia* is added to about 2.0-3.0 g of a mixed blend of elderflower, dandelion root, green tea leaves, lemon balm, crystalized ginger root, and lemon peel. Approximately 16 ounces or 500 ml of this blend is preferably steeped in boiling water for 7-10 minutes using tea sachet. The resulting Herbal THC Detoxification Blend can be immediately administered warm or as a cold drink or stored for later use.

The inventor has found that the most effective use of the plant to maintain its purgative properties is to directly freeze fresh plant material and only thaw before making the decoction, or using the fresh plant itself. Because the main ingredient has to be fresh or frozen, the decoction of blended herbs and *Mormodica charantia* has a shelf life of approximately 3-5 days under standard refrigeration temperatures and up to 7 days if the decoction solution is frozen. It is also contemplated that the Herbal THC Detoxification Blend can be made directly from Aqueous Decoction solution.

Alternatively, as yet another non-limiting example, 500 ml the Aqueous Decoction the *Mamordica charantia* described herein is used in which mixed blend of other ingredients is added. These additional ingredients can include, but are not limited to, elderflower, dandelion root, green tea leaves, lemon balm, crystalized ginger root, and lemon peel. The Aqueous Decoction plus the additional ingredients are then further steeped or boiled. As above, the resulting Herbal THC Detoxification Blend can be immediately administered warm or as a cold drink or stored for later use. The inventor has found that the Herbal THC Detoxification Blend has a shelf life of 12-36 months.

Method of Detoxification

The current invention is also drawn to methods of treating THC intoxication or clearing the bloodstream or urine of an individual of detectable THC or THC metabolites in anticipation of urine or blood test. Typically, several factors must be considered in determining the amount of the Herbal THC Detoxification Blend that must be consumed to clear the body of THC to undetectable limits. Body weight and the amount of THC are two of the most important factors to consider in determining how much consumed would have an impact on how much of the Herbal THC Detoxification Blend is needed to cleanse THC metabolites from the system.

As a non-limiting method to produce a single serving of the Herbal THC Detoxification Blend, 6.0 g of fresh *Momordica charantia* plant is added to about 6.0 g of a mixed blend of elderflower, dandelion root, green tea leaves, lemon balm, crystallized ginger root and lemon peel. Approximately 16 ounces or 500 ml of this blend is preferably steeped in boiling water for 7-10 minutes using a tea sachet. The resulting Herbal THC Detoxification Blend can be immediately administered warm or as a cold drink or stored for later use.

As a non-limiting example, the inventor has found that for moderate THC consumption, 16 ounces or 500 ml of the Herbal THC Detoxification Blend in addition to drinking half body weight of water in ounces throughout cleanse process typically works for the removal of THC or detectable metabolites in the bloodstream and urine.

For heavy consumption of THC, the inventor has found that 32 ounces of the Herbal THC Detoxification Blend is recommended. It was to be advantageous to drink the full 16 ounces of the Herbal THC Detoxification Blend within 1 hour and drinking half body weight in ounces within 4 hours of drinking cleanse. This will allow toxins and detectable THC metabolites to pass through urine. Once urine has a clear color (which typically happens within first 4 hours of drinking the Herbal THC Detoxification Blend), the cleanse is complete.

The inventor has determined that the success of the Herbal THC Detoxification Blend in clearing an individual's system of THC or detectable THC metabolites, also requires that the individual concurrently refrain from using THC or any THC product including so-called edibles.

Monitoring of the Efficacy of the Herbal THC Detoxification Blend

The efficacy can be easily monitored through the use of any commercially available home drug testing kit. It is contemplated that any commercially available test kit from online retailers or medical suppliers can be used. For example, the inventor contemplates that home test kits that test saliva, urine, or hair can be used. Test kits that test for THC or dateable metabolites in urine are preferred as they will typically mimic the tests to be used for employment or other official uses.

If home testing reveals that THC or its metabolites are still detectable, further consumption of the Herbal THC Detoxification Blend can commence. This process can be repeated as many times as necessary until THC or its detectable metabolites are no longer detectable in an individual's urine.

General guidelines suggest that THC metabolites can be detected for up to 90 days the in heavy, daily users without the use of the Herbal THC Detoxification Blend. The rate at which THC metabolites clear from an individual's system depends on their lifestyle, amount of exercise, diet and percentage of body fat. The inventor has found that with the use of the Herbal THC Detoxification Blend, detectable THC and its metabolites can be cleared from an individual's system within 24-48 hours.

Definitions

In the specification and in the claims, the terms "including" and "comprising" are open-ended terms and should be interpreted to mean "including, but not limited to . . . " These terms encompass the more restrictive terms "consisting essentially of" and "consisting of".

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The terms "about" or "approximately" as used herein mean within an acceptable error range for the particular value as determined by one of ordinary skill in the art, which will depend in part on how the value is measured or determined, i.e. the limitations of the measurement system. For example, "about" can mean within 3 or more than 3 standard deviations, per the practice in the art. Alternatively, particularly with respect to biological systems or processes, the term can mean within an order of magnitude, preferably within 5-fold and more preferably within 2-fold, of a value.

The following examples are offered by way of illustration and not limitation.

EXAMPLES

Example 1

*Momordica charantia* Herbal THC Detoxification Blend

Table 1 shows an example of the amount of each ingredient for making the herbal tea blend.

TABLE 1

| Ingredient | To Make a Single Serving |
|---|---|
| Momordica Charantia | 6.0 g |
| Green tea or similar | 3.0 g |
| Elderflower | 1.0 g |
| Dandelion Root | 1.0 g |
| Lemon Balm | 500 mg |
| Ginger Root | 500 mg |
| Water to volume | |
| TOTAL | 8.5 g |

The inventor contemplates that the amount of each ingredient may vary based on amount of detoxification required for example following a light consumption of THC, versus moderate consumption of THC versus heavy consumption of THC.

Example 2

Aqueous Decoction

A non-limiting example of an aqueous decoction is described below. The entire *Momordica charantia* plant is first mashed the plant, without the bitter melon, for maximum dissolution, and then boiling in about 600 ml distilled or spring water. The boiling allows for the extraction of oils, volatile organic compounds and various chemical substances from the plant. The mashed plant was boiled for about 15 minutes.

The bitter melon fruit is then added to the boiled decoction solution in addition to a sliced whole lemon. After decoction is brewed for an additional for about 12-15 minutes, the resulting solution is strained to remove the plant and lemon slices and any other remaining particles.

Once the Aqueous Decoction solution is strained, other ingredients can be added. As a non-limiting example, a sweetener such as stevia is added to improve the taste of the decoction. It is contemplated that the amount and type of sweetener can be varied according to individual preferences.

The resulting Aqueous Decoction solution is typically about 1500 ml. This typically yields about three 500 ml detoxification doses.

TABLE 2

| Ingredient | Amount |
| --- | --- |
| Momordica Charantia | 10.5 g |
| Lemon | 2 slices or to taste |
| Sweetener | to taste |
| Water | to volume |
| TOTAL | 2.0 L |

The resulting solution has a shelf life of one week and can be frozen for up to one week to preserve.

Example 3

Testing Examples

Examples of 2 individuals who were voluntarily administered the Herbal THC Detoxification Blend and their subsequent THC testing results are shown below in Table 3.

TABLE 3

| Individual | Issue | Detoxification Procedure | Results |
| --- | --- | --- | --- |
| Female (28) Pregnant | Required monthly drug tests during course of pregnancy to detect possible drug use; required postpartum urine drug testing weekly for 12 consecutive months. | drink 16 oz of Herbal THC Detoxification Blend 2-6 hrs prior to drug test being administered | All tests showed urine free of THC metabolites despite admitted inhalation and smoking of marijuana. other drugs that were in her system were also traced (e.g. α-pyrrolidinopentiophenone, "flakka," "bath salts) |
| Female (35-50) Diagnosed with Anxiety Disorder | Prescribed various medications for pain (e.g. hydrocodone smokes marijuana to aide with side effects; required monthly urine drug testing to verify compliance with prescription medication and no other drug use | drink 16 ounces of Herbal THC Detoxification Blend 12 hours prior to drug test being administered | All tests showed urine free of THC metabolites despite admitted inhalation and smoking of marijuana. prescription medications not detected due to due to Herbal THC Detoxification Blend |

Although the foregoing invention has been described in some detail by way of illustration and example for purposes of clarity of understanding, it will be obvious that certain changes and modifications may be practiced within the scope of the claims.

I claim:

1. A method for removing tetrahydrocannabinol or its metabolites from an individual's bloodstream and urine comprising ingesting a composition comprising an aqueous decoction of the plant *Momordica charantia*.

2. The method of claim 1, wherein the composition further comprises water and one or more herbs or other natural products.

3. The method of claim 2, wherein the herb or other natural products is selected from the group consisting of the fruit of the *Momordica charantia* plant, elder flower, dandelion root, green tea leaves, lemon balm, lemon peel, crystalized ginger root and a sweetener.

4. The method of claim 1, wherein the composition comprises a solution made from the *Momordica charantia* which has been dried and ground.

5. The method of claim 1, wherein the amount of composition ingested is based upon the body weight of the individual.

6. The method of claim 5, wherein the composition is ingested in one or more times over a period of four hours.

7. The method of claim 1 which is repeated one or more times within a 24 to 48 hour period.

8. The method of claim 1, wherein the efficacy for removing tetrahydrocannabinol or its metabolites from an individual's bloodstream and urine is monitored using a home drug testing kit.

\* \* \* \* \*